United States Patent [19]

Wilkes

[11] 4,096,188

[45] Jun. 20, 1978

[54] PREPARATION OF STRAIGHT CHAIN ALDEHYDES

[75] Inventor: John B. Wilkes, Richmond, Calif.

[73] Assignee: Chevron Research Company, San Francisco, Calif.

[21] Appl. No.: 752,582

[22] Filed: Dec. 20, 1976

[51] Int. Cl.$^2$ ............................................. C07C 45/08
[52] U.S. Cl. ............................................. 260/604 HF
[58] Field of Search .................. 260/604 HF, 632 HF

[56] References Cited

U.S. PATENT DOCUMENTS

| | | | |
|---|---|---|---|
| 2,820,059 | 1/1958 | Haseh et al. | 260/604 HF |
| 3,560,572 | 2/1971 | Deffner et al. | 260/604 HF |
| 3,594,425 | 7/1971 | Brader et al. | 260/604 HF |
| 3,624,158 | 11/1971 | Deffner et al. | 260/604 HF |
| 3,857,893 | 12/1974 | Nazoki | 260/604 HF |
| 3,931,332 | 1/1976 | Wilkes | 260/604 HF |

*Primary Examiner*—James O. Thomas, Jr.
*Assistant Examiner*—Werren B. Lone
*Attorney, Agent, or Firm*—D. A. Newell; John Stoner, Jr.

[57] ABSTRACT

Straight chain aldehydes are prepared from straight chain olefins of about 3 to 20 carbon atoms by catalytic hydroformylation with carbon monoxide and hydrogen in the presence of cobalt catalyst and in the presence of soluble primary, secondary or tertiary aliphatic, or cycloaliphatic amine modifier of 1 to 12 carbon atoms.

7 Claims, No Drawings

PREPARATION OF STRAIGHT CHAIN ALDEHYDES

BACKGROUND OF THE INVENTION

1. Field of the Invention

The present invention relates to the preparation of straight chain aldehydes. More particularly, the invention relates to the preparation of straight chain aldehydes by an amine-modified oxo process.

2. Description of the Prior Art

The preparation of aldehydes by the hydroformylation of olefins, also called the oxo process, is generally known. See, for instance, the chapter on "Oxo Process" in Kirk-Othmer Encyclopedia of Chemical Technology, 2nd Ed., published 1963, in Volume 14, page 373.

The production of straight chain aldehydes from straight chain olefins by the hydroformylation reaction is particularly desirable because of the generally superior performance of products derived therefrom. For example, the aldehydes are readily oxidized to carboxylic acids which by their linearity are useful in the production of synthetic ester lubricants. Also, the aldehydes undergo aldol condensation to give higher aldehydes useful for production of higher alcohols. The straight chain alcohols obtained by hydrogenation of straight chain aldehydes are sulfated to provide superior alkyl sulfate detergents.

It has been suggested that straight chain products may be obtained by the hydroformylation reaction when the usual cobalt catalyst is modified with phosphines, perferably trialkyl or alicyclic phosphines. See, for instance, U.S. Pat. No. 3,239,569.

It has also been suggested that straight chain products may be obtained by the hydroformylation reaction with 1-alkenes with conventional cobalt catalysts at particular temperatures in the range of 60° to 100° C. The reaction is extremely slow below 100° C. See, for instance, U.S. Pat. No. 2,824,344.

The use of weak amines to accelerate the hydroformylation reaction has been suggested, but no effect on the straight chain content was observed. See, for instance, U.S. Pat. No. 2,820,059.

Polyamines such as ethylene diamine have been employed in the preparation of transition metal complexes of unknown nature for catalysts in hydroformylation. See, for instance, U.S. Pat. No. 3,594,425.

Substituted pyridines have been suggested to accelerate the oxo reaction but in general it was found that product linearity was greatly reduced. See, for instance, U.S. Pat. No. 3,231,621.

SUMMARY OF THE INVENTION

In accordance with the present invention there is provided in the catalytic hydroformylation process of preparing straight chain aldehydes from straight chain olefins by the reaction of straight chain olefins of about 3 to 20 carbon atoms with carbon monoxide and hydrogen under hydroformylation conditions in the presence of a cobalt catalyst at a temperature of about 75° to 200° C and a pressure of about 500 to 5000 pounds per square inch, the improvement which comprises carrying out the reaction in the presence of a soluble primary or secondary aliphatic, or cycloaliphatic amine modifier of 1 to 12 carbon atoms, said modifier being present in amounts from about 0.05 to 1 mols of amine per mcl of cobalt.

In the present process the hydroformylation reaction proceeds rapidly. Only very small amounts of the amine modifier are required, preferably from 0.1 to 0.8 mols per mol of cobalt, and most preferably 0.3 to 0.6 mols per mol of cobalt. A further advantage of the present process resides in the fact that it effectively provides straight chain aldehydes not only from straight chain alpha olefins but also from straight chain internal olefins. In the event the reaction with internal olefins is somewhat slower, a conventional accelerator may be suitably combined with the amine modifier. Such straight chain internal olefins are more readily available than straight chain alpha-olefins since they are commonly obtained from n-paraffins by catalytic dehydrogenation, by chlorination-dehydroclorination, or by air oxidation in the presence of boric acid followed by hydrolysis to alcohols and then dehydration.

DESCRIPTION OF THE PREFERRED EMBODIMENTS

In the hydroformylation reaction the straight chain olefin is intimately contacted in the liquid phase with carbon monoxide and hydrogen in the presence of the cobalt catalyst. The hydroformylation conditions include pressures of from about 500 to 5000 pounds per square inch of carbon monoxide and hydrogen. The temperature of the hydroformylation reaction is ordinarily in the range of about 75° to 200° C.

Although the temperature of the reaction may vary from 75° to 200° C, it is preferred to operate at the lower temperatures, in the range of 100° to 150° C and more preferably in the range of 110° to 140° C. Higher temperatures favor the formation of by-products over the formation of aldehydes. At temperatures in excess of about 200° C, high boiling by-product becomes the major product. As usual, the rate of reaction is slower at low temperatures, but the presence of the amine modifier of the instant invention increases the rate permitting good conversions of olefin within the preferred temperature range.

The cobalt catalyst employed in the hydroformylation reaction is a cobalt carbonyl compound which may be formed "in situ" from cobalt salts or chelates. Such cobalt carbonyl compounds include dicobalt octacarbonyl, and cobalt hydrocarbonyl, and the salt $Co[Co(Co)_4]_2$. Cobalt acetate and cobalt acetylacetonate, by way of example, can be used to form the cobalt carbonyl compounds, in situ by reaction with carbon monoxide.

The straight chain olefins contain about 3 to 20 carbon atoms. Representative olefins include propene, 1-butene, 2-butene, 1-pentene, 2-pentene, 1-hexene, 3-hexene, 1-heptene, 2-heptene, 1-octene, 2-octene, 4-octene, 1-decene, 4-decene, 1-undecene, 5-undecene, 1dodecene, 2-tridecene, etc. Mixtures of these olefins may also be used as a feed stock.

The amine modifier of the hydroformylation reaction in accordance with the invention is a primary or secondary aliphatic, or cycloaliphatic monoamines of 1 to 12 carbon atoms. Such amines are soluble in aromatic or aliphatic hydrocarbon solvents such as hexane, benzene, toluene, etc. Illustrative amines include methylamine, dimethylamine, trimethylamine, diethylamine, n-butylamine, benzyl amine, allyl amine, and piperidine.

For present purposes all of such amines may be generically termed "moncamines". From the standpoint of effectiveness n-butylamine and diethylamine in particular have been found satisfactory.

The amount of the amine modifier is critical. As noted above, the art shows that large amounts, e.g. 10 mols of pyridine per mol of cobalt, have been previously observed to decrease the straight chain product from 1-pentene down from 75.6% to 55.6%. Also, it has been found that large amounts of amine generally lower the catalyst activity and even at a mol ratio of 1:1, the rate of reaction is noticeably slower. Accordingly, it is preferred that the modifier in the reaction is present in amounts not exceeding 1 mol of amine per mol of cobalt. Usually at least about one-third mol of amine per mol of cobalt is desirable.

The preparation of straight chain aldehydes in accordance with the process of this invention is further illustrated by the following examples. Unless otherwise indicated, percentages are on a weight basis.

EXAMPLES

EXAMPLE 1A—CONTROL P

To a 300 ml magnetically stirred autoclave was added 3.2 g of a cobalt octoate solution (0.0064 mols Co) and 37.5 g toluene. The reactor was purged with nitrogen, heated to 190° C, pressured to 3600 psig with an equalmolar mixture of CO and $H_2$, and reacted 60 minutes to convert the cobalt salts to catalytically active cobalt carbonyls. The reactor was cooled, and 75 g of 1-octene was added to the catalyst solution.

The reactor was again purged with $N_2$, and $CO+H_2$, and the mixture reacted 90 minutes at 135° C with 3000 psig of a 1:1 mol ratio of CO to $H_2$. The products were cooled and removed and analyzed by gas chromatography.

EXAMPLE 1B

The reactor was charged with 1.6 g of the cobalt octoate solution (0.0032 mols Co), 50 g n-heptane, 50 g of 1-octene, and 0.12 g diethylamine to give a 0.5:1 ratio of amine to Co. The diethylamine acted as a catalyst for cobalt carbonyl formation so prior reaction at 190° C was not required. The mixture was reacted 90 minutes at 135° C at 3000 psig with a 1:1 mol ratio of $H_2$ to CO, and analyzed as before.

Results were:

|  | Mol % | |
|---|---|---|
| Product | 1A | 1B |
| Linear aldehyde | 45.7 | 55.9 |
| Branched aldehydes | 27.4 | 23.1 |
| Total aldehydes | 73.1[a] | 79.0[b] |
| Alcohols | 1.8 | 1.6 |
| Formate esters | 0.4 | 0.6 |
| Paraffin | 2.4 | 2.8 |
| Unreacted olefins | 0.2 | 4.2 |
| Total | 77.9 | 88.2 |
| Heavy products, (by difference) | (22.1) | (11.8) |

[a] 62.5% linear aldehyde
[b] 70.7% linear aldehyde

The percent linear product in run 1A (62.5%) agrees well with the results obtained in non-modified oxo reactions reported by Hughes and Kirshenbaum, (reference: Ind. Eng. Chem. 49, 1999–2003 (1957) incorporated by reference), who obtained a 72% linear product from 1-heptene at 100° C and a 55% linear product from the same olefin at 145° C. Interpolation of these results predicts about 60% linearity at 135° C.

EXAMPLE 2

This example was carried out in the same manner as Example 1B, but 0.24 grams of diethylamine was used in place of 0.12 grams. This was a 1:1 mol ratio of diethylamine:cobalt. The reaction was carried out for the same length of time. The product contained 10.1% unreacted olefin, indicating a slower rate than in Example 1B. On the basis of the converted olefin, the products were:

| Product | Mol % |
|---|---|
| Linear aldehyde | 56.9 |
| Branched aldehyde | 23.7 |
| Total aldehyde | 86.6* |
| Alcohols | 1.8 |
| Paraffin | 3.1 |
| Total | 85.7 |
| Heavy products, by difference | 14.3 |

*70.6% linearity in aldehydes.

Data from several other runs were as follows:

| | | Additive | | Cobalt, | Conditions | | | Rate 1st Half Life, Minutes | Products, Mol % | | | | | Aldehyde Isomers % each position | | | |
|---|---|---|---|---|---|---|---|---|---|---|---|---|---|---|---|---|---|
| | | | Mol Mol Co | Wt. % of Olefin | Temp. °C | Press. psig | Time, Min. | | Alcohol | Aldehyde | Paraffin | Olefin | Thick Oil[d] | (Linear) 1 | 2 | 3 | 4 |
| Ex. | Olefin | Type | | | | | | | | | | | | | | | |
| 3 | 1-octene | None | — | 0.25 | 177 | 1550 | 120 | 3–5 | 55 | 18 | 11 | 0.4 | (19) | 47 | 46 | | 6 |
| 4 | 1-octene | None | — | 0.25 | 191 | 3600 | 100 | ~1 | 14 | 10 | 11 | 0.2 | (63) | 44 | 50 | | 6 |
| 5 | 1-octene[a] | None | — | 0.19 | 177–188 | 3000 | 90 | ~2 | 17 | 48 | 5 | 0 | (18) | 45 | 29 | 13 | 13 |
| 6 | 1-octene[a] | None | — | 0.38 | 110 | 2950 | 120 | ~60 | 0.7 | 71 | 2 | 22 | (4) | 77 | 17 | 4 | 3 |
| 7 | 1-octene[a] | Et$_2$NH | 0.5 | 0.39 | 135 | 3000 | 90 | ~5 | 1.6 | 79 | 3 | 4 | (12) | 71 | 20 | 5 | 4 |
| 8 | 1-octene[a] | Et$_2$NH | 1.0 | 0.39 | 135 | 3000 | 90 | 6–8 | 1.6 | 73 | 3 | 10 | (13) | 71 | 20 | 5 | 5 |
| 9 | 2-octene | Et$_2$NH | 1.0 | 0.50 | 135 | 3000 | 90 | ~10 | 0.9 | 82 | 0.7 | 3 | (13) | 59 | 22 | 10 | 9 |
| 10 | 2-octene | Et$_2$NH | 1.0 | 0.39 | 116 | 3000 | 120 | 10–15 | 0.6 | 51 | 0.7 | 46 | (2) | 63 | 20 | 9 | 8 |
| 11 | 3-heptene[a] | n-BuNH$_2$ | 0.5 | 0.28 | 135 | 3000 | 90 | ~30 | 1 | 75 | 1 | 20 | (3) | 61 | 20 | 13 | 6 |
| 12 | 3-heptene[a] | n-BuNH$_2$ | 0.33 | 0.42 | 135 | 3000 | 90 | ~10 | 1 | 80 | 1 | 14 | (5) | 59 | 20 | 20 | |
| 13 | 3-heptene[a] | n-BuNH$_2$ | 0.33 | 0.38 | 135 | 3000 | 180 | ~20 | 4 | 81 | 1.6 | 0.8 | (13) | 58 | 20 | 22 | |
| 14 | 4-octene[a] | n-Bunh$_2$ | 0.53 | 0.44 | 135 | 3000 | 90 | 15 | 0.6 | 58 | 0.8 | 15 | (26) | 54 | 18 | 12 | 16 |
| 15 | 4-octene[a] | n-BuNH$_2$ | 0.53 | 0.44 | 135 | 2980 | 120 | 30 | 2 | 79 | 6 | (11) | 54 | 18 | 12 | 16 |

[a] 50% solvent
[b] 75% solvent
[c] 66.7% solvent
Solvents varied - heptane, benzene, or toluene
[d] Determined by difference In the above table, Examples 3, 4, 5 and 6 illustrate the results obtained in the absence of the amine modifier of the present invention. These examples show improved straight chain aldehyde yields as the temperature is lowered, but at the same time, the reaction rate decreases until at 110° C, the half-life is 60 minutes. Examples 7 and 8 illustrate the effect of added amine, i.e., the straight chain aldehyde yield is high and the reaction rate is fast, with a half-life of about 5 to 8 minutes. Examples 9 through 15 illustrate straight chain aldehyde yields in the range of 54% to 63% obtained from internal olefins in the presence of the amine modifier. Starting with 2-octene, or 3-heptene, linear aldehyde yields are about 60% (Examples 9–13). On the other hand, the above cited reference of Hughes and Kirshenbaum shows that in the prior art 2-heptene did not give as much as 50% linear product.

While the character of this invention has been described in detail with illustrative examples, this had been done by way of illustration only and without limitation of the invention. It will be apparent to those skilled in the art that modifications and variations of the illustrative examples may be made in the practice of the invention within the scope of the following claims.

I claim:

1. In the catalytic hydroformylation process of preparing straight chain aldehydes from straight chain olefins by the reaction of straight chain olefins of about 3 to 20 carbon atoms with carbon monoxide and hydrogen under hydroformylation conditions in the presence of a cobalt catalyst at a temperature of about 75° to 200° C and a pressure of about 500 to 5000 pounds per square inch, the improvement which comprises carrying out the reaction in the presence of a monoamine modifier consisting essentially of methylamine, dimethylamine, trimethylamine, diethylamine, n-butylamine, benzyl amine, allyl amine, or piperidine, said modifier being present in amounts from about 0.05 to 1.0 mols of amine per mol of cobalt.

2. The process of claim 1 in which the amine modifier is n-butylamine.

3. The process of claim 1 in which the amine modifier is diethylamine.

4. The process of claim 1 in which the straight chain olefin is an internal olefin.

5. The process of claim 1 in which the olefin is 1-octene.

6. The process of claim 1 in which the olefin is a mixture of 85 mol percent 2-octene and 15 mol percent 1-octene.

7. The process of claim 1 in which the temperature is about 100° to 150° C.

* * * * *

UNITED STATES PATENT AND TRADEMARK OFFICE
CERTIFICATE OF CORRECTION

PATENT NO. : 4,096,188
DATED : June 20, 1978
INVENTOR(S) : John B. Wilkes

It is certified that error appears in the above-identified patent and that said Letters Patent are hereby corrected as shown below:

Column 1, line 32, "perferably" should read --preferably--.

Column 2, line 46, "(Co)$_4$" should read --(CO)$_4$--.

Column 3, line 18, "Control P" should read --Control--.

Column 3, example 14, 3rd column of table, "n-Bunh$_2$" should read --n-BuNH$_2$--.

Column 3, under the headings "Products, Mol %" and "Aldehyde Isomers % each position", example 15,
"2   79   6   (11)   54   18   12   16   (blank)" should read --2   79   1   6   (11)   54   18   12   16--.

Signed and Sealed this

Sixth Day of February 1979

[SEAL]

Attest:

RUTH C. MASON
Attesting Officer

DONALD W. BANNER
Commissioner of Patents and Trademarks